(12) United States Patent
Pagani et al.

(10) Patent No.: US 6,334,984 B1
(45) Date of Patent: *Jan. 1, 2002

(54) HYDROLYSIS REACTOR FOR REMOVAL OF UREA, AMMONIA AND CARBON DIOXIDE FROM A LIQUID PHASE COMPRISING UREA IN AQUEOUS SOLUTION

(75) Inventors: Giorgio Pagani, Lugano; Federico Zardi, Breganzona, both of (CH)

(73) Assignee: Urea Casale S.A., Lugano-Besso (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/065,044

(22) PCT Filed: Sep. 27, 1996

(86) PCT No.: PCT/IB96/01004

§ 371 Date: Apr. 27, 1998

§ 102(e) Date: Apr. 27, 1998

(87) PCT Pub. No.: WO97/15388

PCT Pub. Date: May 1, 1997

(30) Foreign Application Priority Data

Oct. 27, 1995 (CH) .............................................. 3033/95

(51) Int. Cl.[7] .............................. B01J 8/04; B01J 10/00
(52) U.S. Cl. ....................... 422/195; 422/188; 422/191; 422/193; 422/194; 422/224; 202/162; 159/47.2
(58) Field of Search ................................ 422/193, 194, 422/195, 192, 191, 189, 188, 224, 227, 230; 564/73, 67, 68, 70; 261/112.2, 113, 114.2, 114.3; 202/158, 162

(56) References Cited

U.S. PATENT DOCUMENTS

| 3,617,033 A | | 11/1971 | Ichikawa | 261/21 |
| 3,917,460 A | * | 11/1975 | Morgan | 422/193 |
| 3,922,147 A | * | 11/1975 | Sze et al. | 422/193 |
| 4,013,560 A | * | 3/1977 | Pradt | |
| 4,341,640 A | | 7/1982 | Landis | 210/752 |
| 5,304,353 A | * | 4/1994 | Dente et al. | 422/193 |

FOREIGN PATENT DOCUMENTS

| EP | 0538848 | 4/1993 |
| EP | 0612560 | 8/1994 |
| GB | 911231 | 11/1962 |
| JP | 63224785 | 1/1989 |

* cited by examiner

Primary Examiner—Hien Tran
Assistant Examiner—Alexa A. Doroshenk
(74) Attorney, Agent, or Firm—Sughrue Mion, PLLC

(57) ABSTRACT

A hydrolysis reactor for removal of urea, ammonia and carbon dioxide from a liquid phase comprising urea in aqueous solution advantageously comprises a dividing baffle extending horizontally at a preset height in the reactor in which it defines a first and a second respectively lower and upper reaction space, means of collection and extraction from the reactor of a first portion of a gaseous phase comprising high pressure and temperature steam, previously fed into the first reaction space and means for feeding a second portion of the gaseous phase comprising high pressure and temperature steam to the second reaction space.

11 Claims, 2 Drawing Sheets

HYDROLYSIS REACTOR FOR REMOVAL OF UREA, AMMONIA AND CARBON DIOXIDE FROM A LIQUID PHASE COMPRISING UREA IN AQUEOUS SOLUTION

DESCRIPTION

1. Field of the Invention

The present invention relates to a hydrolysis reactor for removal of urea, ammonia and carbon dioxide from a liquid phase comprising urea in aqueous solution.

As known, waste waters resulting from the purification and recovery process of urea produced in a high-pressure and temperature synthesis reactor have a high residual urea content in aqueous solution generally between 500 ppm and 30'000 ppm and as such cannot be freely discharged into the environment because of the severe antipollution laws in force in industrialized countries.

Each urea production plant must therefore provide appropriate equipment capable of removing residual urea from the waste water so as to lower its concentration to a few ppm, preferably less than 10 ppm.

In the field of treatment of waste waters resulting from the urea purification and recovery process, the requirement for making available residual urea hydrolysis reactors, which would allow on the one hand to obtain non-polluting waste waters with a urea content less than 10 ppm and on the other hand to recover the residual urea (in the form of ammonia and carbon dioxide) contained in these waste waters fed to the hydrolysis reactor, is thus strongly felt.

2. Prior Art

In order to meet the above mentioned requirement, vertical hydrolysis reactors in which flows a liquid phase comprising urea in aqueous solution and a gaseous phase comprising high pressure and temperature steam, generally between 15 bar and 30 bar and between 150° C. and 250° C., have been becoming more widely used.

These reactors contain a plurality of horizontally extending perforated plates.

The perforated plates have the function of facilitating the mutual mixing of the phases to encourage intimate contact, and thus exchange of mass and heat essential for the hydrolysis reaction of the urea in ammonia ($NH_3$) and carbon dioxide ($CO_2$), and for simultaneous extraction of the $NH_3$ and $CO_2$ from the liquid phase to the gaseous phase.

The heat necessary for decomposition of the urea and extraction of the reaction products from the liquid phase is supplied by the steam contained in the gaseous phase.

Canadian patent application CA-A-2 141 886 describes a reactor of this type in which the liquid phase and the gaseous phase are made to flow in co-current from below upwards through a plurality of horizontal perforated plates.

Although advantageous in many ways, the hydrolysis reactor described above exhibits a number of drawbacks, the first of which is that to obtain the desired degree of decomposition of the urea and related extraction from the liquid phase of the $NH_3$ and the $CO_2$ produced, it is necessary to operate with excess of steam to prevent the hydrolysis reaction from reaching the equilibrium before its time and the gaseous solution from becoming saturated with the reaction products already during its passage through the reactor.

As a result, to obtain an aqueous solution with a residual urea content lower than 10 ppm it is necessary to use high quantities of high pressure and temperature steam, with the ensuing high energy and steam consumption and high operation costs.

SUMMARY OF THE INVENTION

The technical problem underlying the present invention is to make available a hydrolysis reactor for removal of urea, ammonia and carbon dioxide from a liquid phase comprising urea in aqueous solution, which would permit operation with low steam and energy consumption and low liquid phase with a urea content below 10 ppm.

In accordance with a first embodiment of the present invention, the above mentioned problem is solved by a hydrolysis reactor for removal of urea, ammonia and carbon dioxide from a liquid phase comprising urea in aqueous solution, comprising:

a substantially cylindrical vertical external shell;

a plurality of perforated plates superimposed and extending horizontally and in mutually spaced relationship in said shell;

an inlet opening for said liquid phase arranged proximate to a lower end of said shell;

first means of supplying a first portion of a gaseous phase comprising high pressure and temperature steam, supported in said shell above said liquid phase inlet opening;

an outlet opening for said liquid phase arranged proximate to an upper end of said shell;

an outlet opening for said gaseous phase arranged proximate to the upper end of said shell; and characterized in that it comprises:

a dividing baffle extending horizontally at a preset height in said shell, in which it defines a first and a second respectively lower and upper reaction space;

means of collection and extraction from the shell of said first gaseous phase portion, supported proximate to said dividing baffle in said first reaction space;

second means of feeding a second portion of said gaseous phase comprising high pressure and temperature steam, supported above said dividing baffle in said second reaction space.

Advantageously, in the hydrolysis reactor according to the present invention, the reaction space in the shell is appropriately divided by a dividing baffle in a first and a second reaction space each of which is fed with a respective gaseous phase portion comprising steam.

In this manner it is possible to use efficiently and rationally the high pressure and temperature steam necessary for decomposition of the urea and extraction of the reaction products, so as to obtain, for equal liquid phase purification degree, a substantial reduction of the quantity of steam to be fed into the hydrolysis reactor with respect to prior art reactors.

Indeed, thanks to the present invention, purification of the liquid phase takes place appropriately in two distinct reaction spaces, into each of which is fed the quantity of steam strictly necessary for obtaining a liquid phase outlet from the hydrolysis reactor with a residual urea concentration below 10 ppm.

In particular, extraction from the first reaction space of the gaseous phase now saturated with reaction products and feeding into the second reaction space of a new gaseous phase comprising high pressure and temperature steam, permit hydrolysis also of the last traces of urea contained in the liquid phase as well as recovery of the $NH_3$ and $CO_2$ in the gaseous phase without thereby having to employ excess of steam.

The liquid phase thus purified can be discharged into the environment but can also be advantageously reused as high temperature and pressure water in the urea synthesis plant or for other industrial uses, e.g. as boiler water.

Another advantage of the hydrolysis reactor which is the object of the present invention lies in the fact that, for equal residual urea concentration contained in the outlet liquid phase, the residence time of the liquid phase in the reactor is significantly lower than the residence time in the prior art reactors.

This permits building a hydrolysis reactor with dimensions and investment costs considerably less than those of the prior art.

Particularly advantageous results were found by arranging the dividing baffle at a height between 55% and 80% of the useful height of the shell.

In the description given below and in the following claims, the term "useful height", is understood to mean the height of the shell usable for the urea hydrolysis reaction. In this particular case the useful height is defined by the level reached by the liquid phase in the shell.

Preferably, the dividing baffle is arranged at a height between 65% and 75% of the useful shell height.

In this manner, there is obtained with small amounts of high pressure and temperature steam and low operating costs, a concentration of urea in liquid phase in the first reaction space generally between 30 ppm and 70 ppm and in the second reaction space between 0 ppm and 5 ppm.

In accordance with this first embodiment of the present invention, the hydrolysis reactor includes advantageously a dividing baffle extending horizontally for substantially the entire cross section of the shell.

In addition, the collection and extraction means comprise advantageously:

a collection chamber for the first gaseous phase portion, formed in the first reaction space between the dividing baffle and an inner wall of the shell;

a duct extending coaxially in the shell between the collection chamber and the gaseous phase outlet opening, for extraction from the first reaction space of a two-phase gas/liquid flow.

As a result, practical implementation of the present invention is simple in construction and of low realization cost.

Advantageously, the hydrolysis reactor comprises in addition a gas/liquid separator placed between the extraction duct and the gaseous phase outlet opening, so that the liquid phase if any entrained in the gaseous phase leaving the reactor can be recycled to the reactor and thus permit recovery of the urea contained therein.

In accordance with a second embodiment of the present invention, the above mentioned problem is also solved by a hydrolysis reactor for removal of urea, ammonia and carbon dioxide from a liquid phase comprising urea in aqueous solution, comprising:

a substantially cylindrical vertical external shell;

a plurality of perforated superimposed plates extending horizontal and in mutually spaced relationship in the shell;

an inlet opening of said liquid phase arranged proximate to a lower end of said shell;

first means for feeding a first portion of a gaseous phase comprising high pressure and temperature steam, supported in said shell above said liquid phase inlet opening;

an outlet opening for said gaseous phase arranged proximate to an upper end of the shell; and characterized in that it comprises:

a dividing baffle extending horizontally in the shell at a preset height and for substantially the entire cross section of the shell, with the baffle defining in said shell a first and a second respectively lower and upper reaction space;

a collection chamber for said first gaseous phase portion, formed in said first reaction space between said dividing baffle and an inner wall of said shell;

a duct extending coaxially in the shell between said collection chamber and said gaseous phase outlet opening, for extraction from said first reaction space of a two-phase gas/liquid flow;

second means of feeding a second portion of said gaseous phase comprising high pressure and temperature steam, supported above said dividing baffle in said second reaction space;

an outlet opening for said liquid phase arranged in said second reaction space proximate to and above said dividing baffle.

Advantageously, in this embodiment of the present invention the liquid phase and the gaseous phase are made to flow in counter-current in the second reaction space.

In this manner, it is possible to further improve the mixing of the phases and hence mass and heat exchange so as to facilitate the urea hydrolysis reaction and absorption of the reaction products by the steam.

The characteristics and advantages of the hydrolysis reactor according to the invention are set forth in the description of an embodiment thereof given below by way of non-limiting example with reference to the annexed drawings.

BRIEF DESCRIPTION OF THE DRAWINGS

In the drawings:

FIG. 3 shows a longitudinal cross section in enlarged scale of a detail of the hydrolysis reactor of FIG. 1.

DETAILED DESCRIPTION OF A PREFERRED EMBODIMENT

Figure 1:
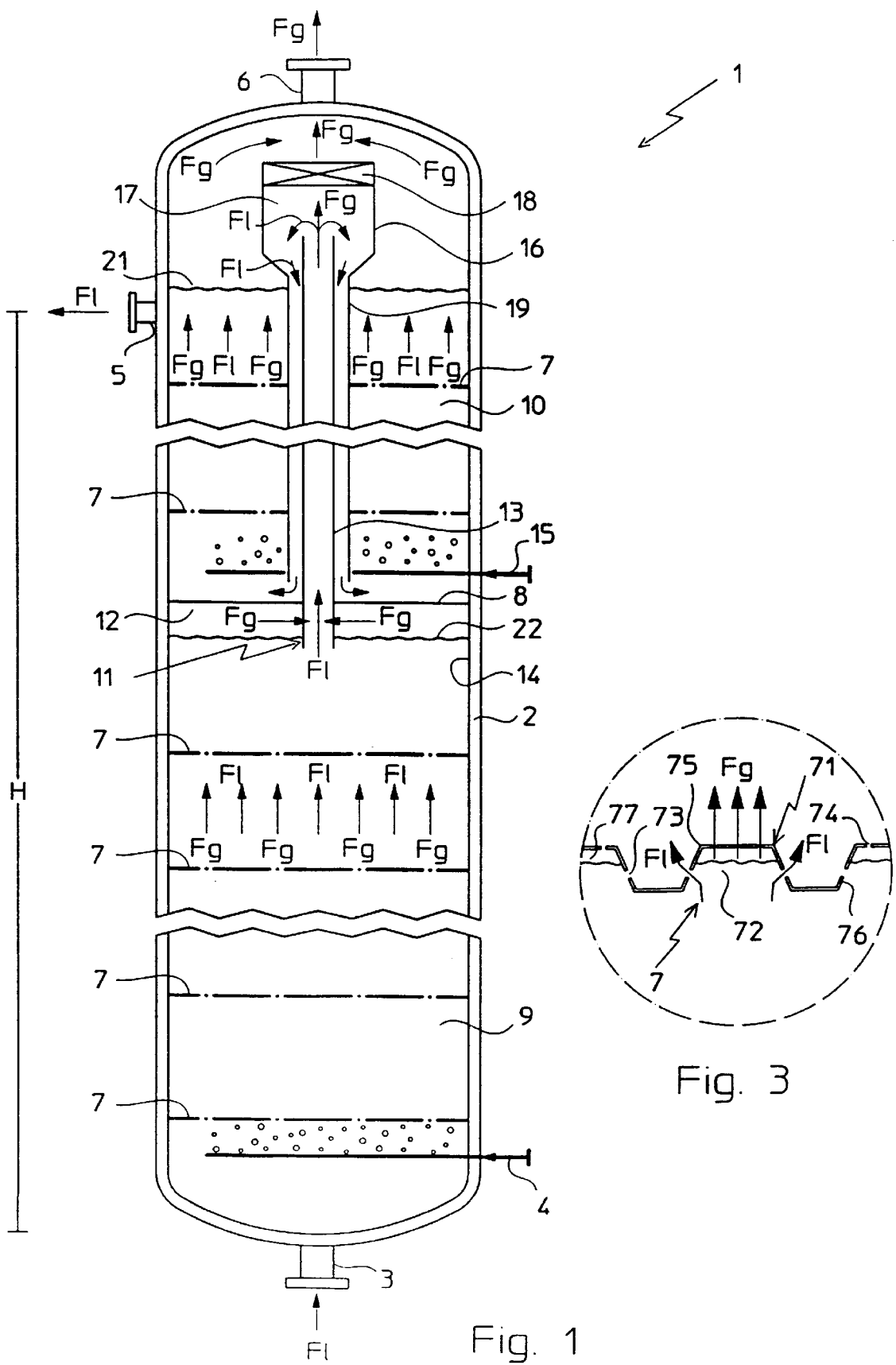
FIG. 1 shows a longitudinal cross section of a urea hydrolysis reactor according to a first embodiment of the present invention.
Figure 2:
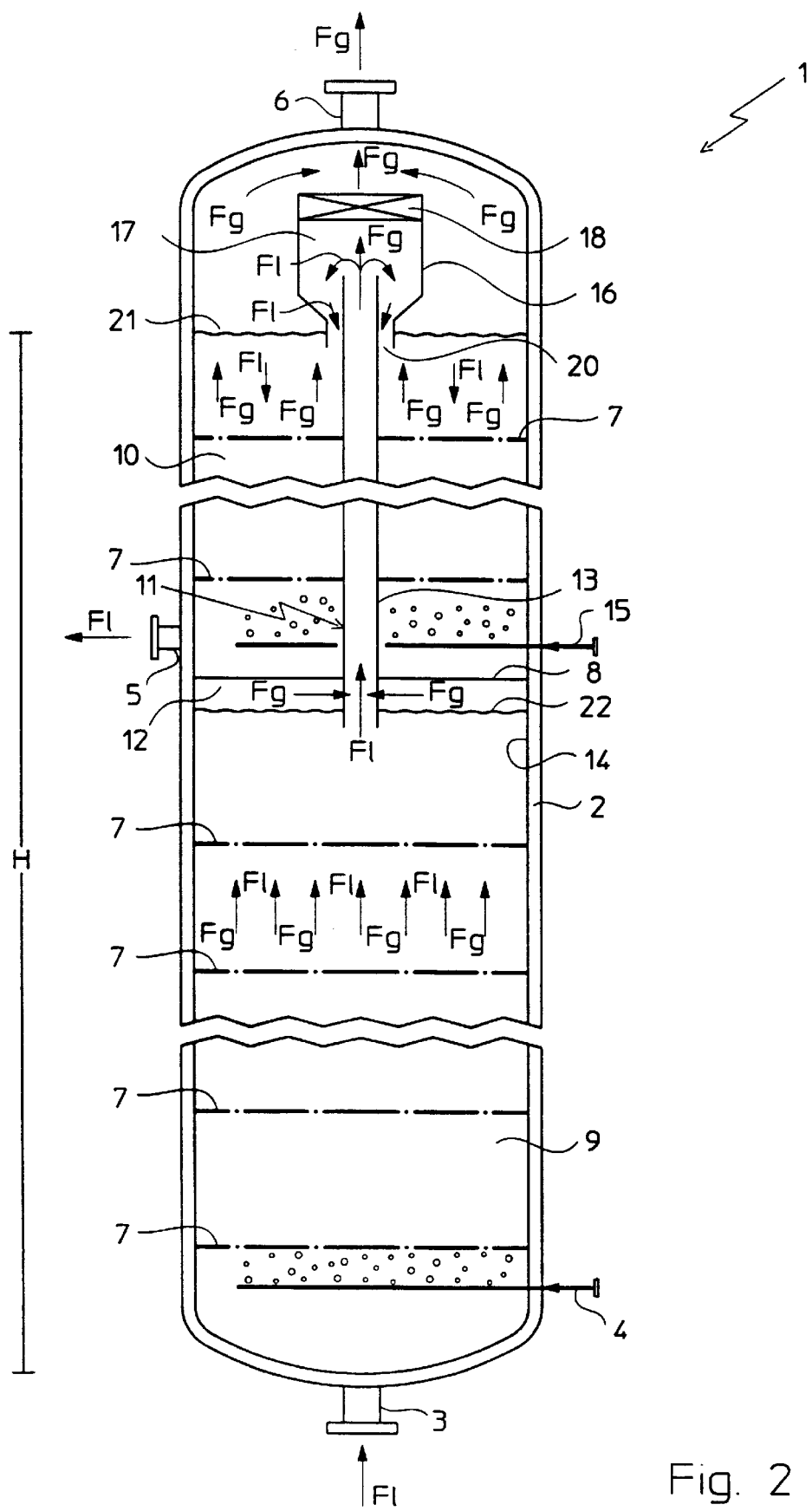
FIG. 2 shows a longitudinal cross section of a urea hydrolysis reactor according to a second embodiment of the present invention.

With reference to FIGS. 1 and 2, reference number 1 indicates as a whole a hydrolysis reactor for removal of urea, ammonia and carbon dioxide from a liquid phase comprising urea in aqueous solution.

The reactor 1 comprises a substantially cylindrical vertical external shell 2, provided at its lower end with an inlet opening 3 for a liquid phase comprising urea in aqueous solution, and with means 4 for feeding a first portion of a gaseous phase comprising high pressure and temperature steam.

The shell 2 also has a liquid phase outlet opening 5 and a gaseous phase outlet opening 6 arranged at an upper end of the reactor.

A plurality of superimposed perforated plates, all indicated by reference number 7, extend horizontally and in mutually spaced relationship in the shell 2.

The plates 7 are homogeneously distributed along the useful height H of the shell, and are provided with appropriate passages for the liquid phase and the gaseous phase to facilitate mixing of the phases.

FIG. 3 shows in enlarged scale a detail of a perforated plate 7, provided according to a particularly advantageous and preferred embodiment of the present invention, which can be installed into the hydrolysis reactor shown in FIG. 1, as well as in the reactor of FIG. 2.

The perforated plate 7 comprises a plurality of elements 71 with substantially trapezoid cross section, defining within them respective cavities 72, as well as appropriate openings 73 and 74 for passage of the liquid and gaseous phases respectively.

Alternatively, the element 71 can have a substantially rectangular cross section.

The gaseous phase passage openings 74 are defined in an upper wall 75 of the elements 71.

The liquid phase passage openings 73 are defined in a side wall 76 of the elements 71.

Advantageously the liquid phase passage openings 73 have a size greater than that of the openings 74 for passage of the gaseous phase.

In the description given below and in the following claims, the term "size", is understood to mean the cross section area of an opening.

In the cavity 72 proximate to the wall 75 there is advantageously defined a gaseous phase collection zone 77.

Thanks to this particular structure of the plates, the gaseous phase is separated from the liquid phase during the passage through the plates, to then be again mixed with the liquid phase in finely distributed form.

In this manner it is possible to obtain a significant improvement in the mixing of the phases during their passage through the hydrolysis reactor.

This involves another reduction of the quantity of steam necessary for performance of the hydrolysis and extraction of the reaction products, as well as of the residence time of the liquid phase in the reactor, with resulting reduction of the reactor dimension, of the steam and energy consumption and of the operating and investment costs compared to the prior art reactors.

Plates of this type are described for instance in U.S. Pat. No. 304,353, with reference to a urea synthesis reactor.

Reference number 8 indicates a dividing baffle extending horizontally at a predetermined height of the shell 2. The baffle 8 defines in the shell a first reaction space 9 and a second reaction space 10, respectively lower and upper.

Advantageously, the dividing baffle 8 extends horizontally for substantially the entire cross section of the shell 2.

In the examples of FIGS. 1 and 2, significantly reduced consumption of high pressure and temperature steam is achieved by arranging the dividing baffle 8 at a height corresponding to approximately 70% of the useful height H of the shell 2.

Means 11 for collection and extraction from the shell 2 of the first gaseous phase portion are supported proximate to the dividing baffle 8 in the first reaction space 9.

The means 11 comprise advantageously a chamber 12 for collection of the first gaseous phase portion and a duct 13 for extraction from the first reaction space 9 of a two-phase gas/liquid flow.

The collection chamber 12 is formed in the first reaction space 9 between the dividing baffle 8 and an inner wall 14 of the shell 2.

The extraction duct 13 is equipped with respective gaseous and liquid phase inlet openings and extends coaxially in the shell 2, between the collection chamber 12 and the gaseous phase outlet opening 6.

A second portion of the gaseous phase comprising high pressure and temperature steam is fed to the reactor by appropriate means 15 supported above the dividing baffle 8 in the second reaction space 10.

Preferably, the feeding means 4 and 15 for the gaseous phase are the type comprising a feed duct connected to a gas distributor in the shell 2. These means are generally known and commonly used in prior art hydrolysis reactors.

With reference to FIG. 1, the liquid phase outlet opening 5 is arranged in the second reaction space 10 proximate to the upper end of the shell 2. In the example of FIG. 2, the liquid phase outlet opening 5 is arranged in the second reaction space 10 proximate to and above the dividing baffle 8.

As shown in FIGS. 1 and 2, the hydrolysis reactor according to the present invention comprises advantageously a gas/liquid separator 16 placed between the extraction duct 13 and the gaseous phase outlet opening 6.

The gas/liquid separator 16 is of the type comprising a chamber 17, coaxial with the extraction duct 13, for separation of the liquid phase from the gaseous phase and a demister 18 for separation of the residual liquid phase contained in the gaseous phase leaving the chamber 17.

In the example of FIG. 1, the liquid phase obtained in the gas/liquid separator 16 is advantageously recycled to the second reaction space 10 by means of a recycling duct 19 extending outside and coaxially with the extraction duct 13 between the separation chamber 17 and the dividing baffle 8. In the example of FIG. 2, the recycling takes place through a liquid passage 20.

In FIGS. 1 and 2, the arrows Fl and Fg indicate the various paths inside the hydrolysis reactor of the liquid phase comprising urea in aqueous solution and of the gaseous phase comprising high pressure and temperature steam respectively.

Reference number 21 also indicates the highest level reached by the liquid phase in the shell 2, while 22 indicates the liquid phase level in the collection chamber 12.

Operation of the hydrolysis reactor according to the present invention is as follows.

With reference to FIG. 1, a liquid phase comprising urea in aqueous solution is fed to the reactor 1 through the inlet opening 3, and caused to flow in co-current from below upward with a first gaseous phase portion comprising high-pressure (20–25 bar) and high-temperature (200–220° C.) steam along a first reaction space 9 in the shell 2. The gaseous phase is fed to the reactor 1 through the feeding means 4.

In the reaction space 9, the liquid phase and the gaseous phase are mixed together while passing through the perforated plates 7, so that part of the urea present in aqueous solution is hydrolyzed and the resulting reaction products ($NH_3$ and $CO_2$) are extracted from the steam present in the gaseous phase. In this first reaction space, the concentration of urea in the liquid phase fed to the reactor is advantageously lowered to a value generally comprised between 40 ppm and 50 ppm.

Proximate to the dividing baffle 8, the liquid phase and the first gaseous phase portion are advantageously collected in the chamber 12 and conveyed by the duct 13 to the separation chamber 17 of the gas/liquid separator 16.

In the chamber 17, the liquid phase coming from the first reaction space 9 is separated from the gaseous phase and recirculated to the second reaction space 10 near the dividing baffle 8 through the duct 19.

The gaseous phase, once separated from the liquid phase in the chamber 17, passes through the demister 18 and leaves the reactor 1 through the outlet opening 6.

In the second reaction space 10, the liquid phase is made to flow (still in co-current) with a second portion of the gaseous phase comprising high pressure and temperature steam.

After passing through the perforated plates 7 and reaching the level 21, the liquid phase leaves the reactor 1 through the outlet opening 5. The urea concentration in the liquid phase coming out of the second reaction space 10 is advantageously less than 10 ppm.

In turn, the second gaseous phase portion which has traversed the second reaction space 10 and is enriched with $NH_3$ and $CO_2$, leaves the reactor 1 through the outlet opening 6.

With reference to FIG. 2, the liquid phase coming from the first reaction space 9 and separated in the chamber 17 of the gas/liquid separator 16 is advantageously recycled through the passage 20 to the second reaction space 10 near the level 21.

In accordance with this embodiment of the present invention, the liquid phase flows into the second reaction space 10 from above downward in counter-current with the second gaseous phase portion, to then leave the reactor 1 through the outlet opening 5 placed proximate to the dividing baffle 8.

The hydrolysis reactor according to the present invention operates at a pressure between 15 bar and 25 bar and a temperature between 180° C. and 215° C. The residence time of the liquid phase in the first reaction space is preferably between 20 min and 40 min, while in the second reaction space it is preferably between 10 min and 20 min.

EXAMPLE 1

In the following example a comparison is made of the quantity of high pressure and temperature steam necessary to obtain a residual urea concentration in the waste waters below 10 ppm, in the case where a prior art hydrolysis reactor or a hydrolysis reactor according to the various embodiments of the present invention are used. Reference is made to FIGS. 1 and 2.

The hydrolysis reactors considered have the following dimensions.

Inner shell diameter: 1.5 m

Useful height: 14.0 m

Operating conditions in the reactor are as follows.

Pressure: 20 bar

Temperature: 210° C.

The reactors contain 10 horizontal perforated plates distributed along the useful height of the cylindrical shell.

In the reactors according to the present invention, the dividing baffle is advantageously arranged at approximately 68% of the useful shell height, between the sixth and seventh perforated plates. For further structural details of these reactors reference is made to FIGS. 1 and 2 and related description.

In the prior art reactor, as in that according to the first embodiment of the present invention (FIG. 1), the liquid and gaseous phases are caused to flow in co-current from below upward through the perforated plates. In the second reaction space of the reactor according to the second embodiment of the present invention (FIG. 2), the liquid phase and the gaseous phase flow in counter-current.

The hydrolysis reactors are fed with 30,000 kg/h of a liquid phase having the following composition.

$NH_3$ 10,000 ppm $CO_2$ 2,000 ppm

UREA 10,000 ppm $H_2O$ the rest

The hydrolysis reactors are also fed with a gaseous phase comprising steam at a pressure of 25 bar and a temperature of 215° C.

To obtain a residual urea concentration of 1 ppm in the liquid phase coming out of the reactor, steam consumption in the various cases is shown below.

In the reactor according to the prior art 30 kg of steam are used for 1,000 kg of liquid phase treated.

In the reactor of FIG. 1, 22 kg of steam were used for 1,000 kg of liquid phase treated.

In the reactor of FIG. 2, 20 kg of steam were used for 1,000 kg of liquid phase treated.

As may be noted, thanks to the present invention it is possible to achieve a significant steam consumption reduction, equal to approximately 30% of the steam consumption necessary in the prior art hydrolysis reactor. This also results in a substantial lowering of energy consumption and operating costs.

The results of the present example were achieved by means of calculation algorithms available in trade.

From the above discussion there emerge clearly the numerous advantages achieved by the hydrolysis reactor according to the present invention. In particular, there is achieved a reduction in the residual urea concentration contained in the waste waters at values below 10 ppm as well as recovery of the hydrolyzed urea, while operating with low steam and energy consumption and low operating and investment costs.

What is claimed is:

1. Hydrolysis reactor for removal of urea, ammonia and carbon dioxide from a liquid phase comprising urea in aqueous solution; comprising:

a substantially cylindrical vertical external shell (2);

a plurality of perforated plates (7) superimposed and extending horizontally and in mutually spaced relationship in said shell (2) throughout its height;

a liquid phase inlet opening arranged proximate to a lower end of said shell (2);

first means (4) for feeding a first portion of a gaseous phase comprising high pressure and temperature steam, supported in said shell (2) above said liquid phase inlet opening (3); and a gaseous phase, outlet opening arranged proximate to an upper end of said shell (2);

characterized in that the hydrolysis reactor comprises:

a dividing baffle (8) extending horizontally in said shell (2) at a preset height for substantially the entire cross section of the shell (2), with said baffle defining in said shell (2) a first and a second respectively lower and upper reaction space (9, 10);

a collection chamber (12) for said first gaseous phase portion formed in said first reaction space (9) between said dividing baffle (8) and an inner wall (14) of said shell (2);

a duct (13) extending coaxially in said shell (2) between said collection chamber (12) and said gaseous phase outlet opening (6), for extraction from said first reaction space (9) of a two-phase gas/liquid flow, wherein said duct also extends for a predetermined length in the lower reaction space and is equipped with respective gaseous and liquid phase inlet openings;

second means (15) for feeding a second portion of said gaseous phase comprising high pressure and temperature steam, supported above said dividing baffle (8) in said second reaction space (10);

an outlet opening (5) for said liquid phase arranged in said second reaction space (10) proximate to and above said dividing baffle (8).

2. Reactor according to claim 1, characterized in that said dividing baffle (8) is arranged in said shell (2) at a height between 55% and 80% of the useful height (H) of the shell (2).

3. Reactor according to claim 2, characterized in that said dividing baffle (8) is arranged in said shell (2) at a height between 65% and 75% of the useful height (H) of the shell (2).

4. Reactor according to claim 1, characterized in that it comprises a gas/liquid separator (16) placed between said extraction duct (13) and said gaseous phase outlet opening (6), for separation of the liquid phase from said two-phase flow.

5. Reactor according to claim 4, characterized in that said gas/liquid separator (16) comprises:

a chamber (17) for separation of the liquid phase from the gaseous phase, coaxial with said extraction duct 13;

a demister (18) for separation of the residual liquid phase contained in the gaseous phase coming out of said separation chamber (17);

a liquid passage (20) for recycling of the liquid phase to the second reaction space (10).

6. Reactor according to claim 1, characterized in that said perforated plates (7) comprise:

a plurality of elements (71) with substantially trapezoid or rectangular cross section, defining within them respective collection zones (77) for said gaseous phase;

a plurality of openings (73) for passage of said liquid phase and defined in association with a side wall (76) of said elements (71), and a plurality of openings (74) for passage of said gaseous phase and defined in an upper wall of said elements (71) in fluid communication with said collection zones (77); with said openings (73) for passage of the liquid phase having a size greater than that of said openings (74) for passage of the gaseous phase.

7. Hydrolysis reactor for removal of urea, ammonia and carbon dioxide from a liquid phase comprising urea in aqueous solution, comprising:

a substantially cylindrical vertical external shell (2);

a plurality of perforated plates (7) superimposed and extending horizontally in mutually spaced relationship within said shell (2) throughout its height;

a liquid phase inlet opening arranged proximate to a lower end of said shell (2);

first means (4) for feeding a first portion of a gaseous phase comprising high pressure and temperature steam, supported in said shell (2) above said liquid phase inlet opening (3);

an outlet opening (6) for said gaseous phase arranged proximate to said upper end of said shell (2);

characterized in that the hydrolysis reactor comprises:

a dividing baffle (8) extending horizontally in said shell (2) at a present height for substantially the entire cross section of the shell (2), with said baffle defining in said shell (2) a first and a second respectively lower and upper reaction space (9, 10);

a liquid phase outlet opening arranged proximate to an upper end of said upper reaction space of said shell (2);

a collection chamber (12) for said first gaseous phase portion formed in said first reaction space (9) between said dividing baffle (8) and an inner wall (14) of said shell;

an extraction duct (13) extending coaxially in said shell (2) between said collection chamber (12) and said gaseous phase outlet opening (6) for extraction from said first reaction space (9) of a two-phase gas/liquid flow;

a separate chamber (17) located between said extraction duct (13) and said gaseous phase outlet opening (6), for separating the liquid phase from the gaseous phase of said two-phase flow;

a recycling duct (19) extending outside and coaxially with said extraction duct (13) between said separation chamber (17) and said dividing baffle (8), for recycling proximate to and above said dividing baffle (8) the liquid phase obtained in said separator (16);

a second means (15) for feeding a second portion of said gaseous phase comprising high pressure and temperature steam, supported above said dividing baffle (8) in said second pressure and temperature steam, supported above said dividing baffle (8) in said second reaction space (10).

8. Reactor according to claim 7, characterized in that said dividing baffle (8) is arranged in said shell (2) at a height between 55% and 80% of the useful height (H) of the shell (2).

9. Reactor according to claim 8, characterized in that said dividing baffle (8) is arranged in said shell (2) at a height between 65% and 75% of the useful height (H) of the shell (2).

10. Reactor according to claim 7, further comprising a demister for separation of the residual liquid phase contained in the gaseous phase coming out of said separation chamber.

11. Reactor according to claim 7, characterized in that said perforated plates (7) comprise:

a plurality of elements (71) with substantially trapezoid or rectangular cross section, defining inside them respective collection zones (77) for said gaseous phase;

a plurality of openings (73) for passage of said liquid phase defined in association with a side wall (76) of said elements (71);

a plurality of openings (74) for passage of said gaseous phase defined in an upper wall of said elements (71) in fluid communication with said collection zones (77);

with said openings (73) for passage of the liquid phase having a size greater than that of said openings (74) for passage of the gaseous phase.

* * * * *